United States Patent [19]

Ehrlich et al.

[11] Patent Number: 4,727,498

[45] Date of Patent: Feb. 23, 1988

[54] PROCESS FOR SEGMENTING RESERVOIR PORES

[75] Inventors: Robert Ehrlich; Sterling J. Crabtree, Jr., both of Columbia, S.C.

[73] Assignee: University of South Carolina, Columbia, S.C.

[21] Appl. No.: 666,769

[22] Filed: Oct. 31, 1984

[51] Int. Cl.[4] .......................... G01J 3/46; G01N 15/00
[52] U.S. Cl. .................................. 364/526; 356/402; 364/422
[58] Field of Search ............... 364/525, 526, 416, 420, 364/422; 358/107, 903, 31, 106; 382/1, 17; 356/402, 416, 419; 166/254, 250, 252; 73/643, 151; 436/5, 27; 128/664, 665, 633

[56] References Cited

U.S. PATENT DOCUMENTS

| | | | |
|---|---|---|---|
| 3,973,725 | 3/1976 | Watanabe et al. | 364/416 |
| 3,999,047 | 12/1976 | Green | 364/416 |
| 4,060,713 | 11/1977 | Golaz | 364/416 |
| 4,125,828 | 11/1978 | Reshick et al. | 364/416 |
| 4,146,788 | 3/1979 | Mirkin et al. | 250/253 |
| 4,170,987 | 10/1979 | Anselmo et al. | 128/665 |
| 4,249,827 | 2/1981 | DiMatteo et al. | 356/402 |
| 4,414,635 | 11/1983 | Gast et al. | 364/526 |
| 4,488,245 | 12/1984 | Dalke et al. | 364/526 |
| 4,494,875 | 1/1985 | Schramm et al. | 356/402 |
| 4,503,555 | 3/1985 | Brimhall, Jr. et al. | 364/518 |
| 4,628,468 | 12/1986 | Thompson et al. | 364/422 |

OTHER PUBLICATIONS

M. Goldberg and S. Shlien, A Four-Dimensional Histogram Approach to the Clustering of LANDSAT Data, *Canadian Journal of Remote Sensing*, 2, 1976, 1-11.

R. Ohlander, K. Price, and D. R. Reddy, Picture Segmentation Using a Recursive Region Splitting Method, *Comp. Graph. and Image Proc.*, 8, 1978, 313-333.

B. J. Schacter, L. S. Davis, and A. Rosenfeld, Scene Segmentation by Cluster Detection in Color Spaces, *Sigart Newsletter* No. 58, 1978, 16-17.

Y. Ohta, T. Kanade, and T. Sakai, Color Information for Region Segmentation, *Comp. Graph. and Image Proc.*, 13, 1980, 222-241.

*Primary Examiner*—Errol A. Krass
*Assistant Examiner*—Daniel W. Juffernbruch
*Attorney, Agent, or Firm*—Brumbaugh, Graves, Donohue & Raymond

[57] ABSTRACT

Light transmitted through a thin section of reservoir rock whose pores are filled with blue-dyed epoxy is passed sequentially through red, blue and green filters and the density levels in the filtered images thereafter converted into pixels. The intensity, hue and saturation are then calculated from the red, blue and green components in each scene pixel. From the calculated values of intensity, hue and saturation, the pixels representative of pores and pores underlain by mineral are separated from the non-pore representative pixels.

7 Claims, 2 Drawing Figures

PROCESS FOR SEGMENTING RESERVOIR PORES

BACKGROUND OF THE INVENTION

This invention relates to the segmentation of different phases or states in solids and, more particularly, to the segmentation of pores and minerals in sections of reservoir rocks.

The invention of this application relates to the subject matter of our co-pending application entitled "Analysis of Reservoir Pore Complexes," Ser. No. 524,022, filed Aug. 17, 1983, now abandoned in favor of 16,495.

As disclosed in our co-pending application, petrographic image analysis relates to the characterization of images obtained with a transmitted light microscope from 30 micron petrographic thin sections whose pores are impregnated with blue-dyed epoxy. The thin sections scene is digitized through red, green and blue filters having known spectral characteristics. The filters provide the maximum enhancement to the blue-dyed epoxy-filled pores while leaving the background mineral matrix of non-pores relatively unchanged. A blue dye is chosen because there are few, if any, naturally occurring blue constituents within reservoir rocks.

The mode of illumination is transmitted light rather than reflected light. This results in a scene with a high range of intensity as well as, generally, a high average intensity. Except for those representing opaque objects, most of the pixels have relatively small variation in the intensity values of the three primary color components. Segmentation based on intensity values alone, as disclosed in application Ser. No. 524,022 can lead to misidentification of pixels representing pores and pixels representing non-pores.

Segmentation of pores for the purpose of petrographic analysis must not only identify the pores but precisely define the edges of the pores in order to assure that such features as pore geometry and pore proportion are accurately measured. Segmentation must also be accomplished quickly because many thousands of scenes, each containing as many as one hundred or more pores, must be processed in a typical investigation.

Also, it is desirable that only the portion of the pore that is on the surface of the thin section be identified as a pore in the segmentation process. Because thin sections have a defined thickness, there is often a shelving effect where the edge of the pore is underlain with or overlain by mineral material. Differentiation between the two different types of shelves is necessary to assure that only the pore overlaying the shelf is segmented along with the solid pore.

Prior art segmentation techniques are described in the following articles and publications:

1. R. Ohlander, K. Price, and D. R. Reddy, Picture Segmentation Using a Recursive Region Splitting Method, *Comp. Graph. and Image Proc.*, 8, 1978, 313-333.

2. M. Goldberg and S. Shlien, A Four-Dimensional Histogram Approach to the Clustering of LANDSAT Data, *Canadian Journal of Remote Sensing*, 2, 1976, 1-11.

3. B. J. Schacter, L. S. Davis, and A. Rosenfeld, Scene Segmentation by Cluster Detection in Color Spaces, SIGART Newsletter No. 58, 1978, 16-17.

4. R. B. Ohlander, Analysis of Natural Scenes, Department of Computer Science, Ph.D. Thesis, Carnegie-Mellon University, 1975.

5. A. Ruter, H. Harms, and H. M. Aus, Standardized Color Measurement in Automated Cytophotometry with the Light Microscope, *Pattern Recognition*, 13, 1981, 135-323.

6. Y. Ohta, T. Kanade, and T. Sakai, Color Information for Region Segmentation, *Comp. Graph. and Image Proc.*, 13, 1980, 222-241.

SUMMARY OF THE INVENTION

It is accordingly an object of this invention to provide a process and apparatus therefor for correctly identifying the pores in a rock sample.

It is a further object of the present invention to provide a process and apparatus therefor for segmenting the pores and the pores overlying mineral from the minerals in a rock sample.

These and other objects of the present invention are accomplished by a process in which the light transmitted through a thin section of reservoir rock whose pores are filled with a dyed epoxy is passed sequentially through red, blue and green filters and the density levels in the filtered images thereafter converted into picture elements or pixels. The intensity, hue and saturation are then calculated from the red, blue and green components in each scene pixel. From the calculated values of intensity, hue and saturation, the pixels representative of pores, pores overlain by mineral and pores underlain by mineral are separated from the non-pore representative pixels.

DETAILED DESCRIPTION OF THE PREFERRED EMBODIMENT

Figure 1:
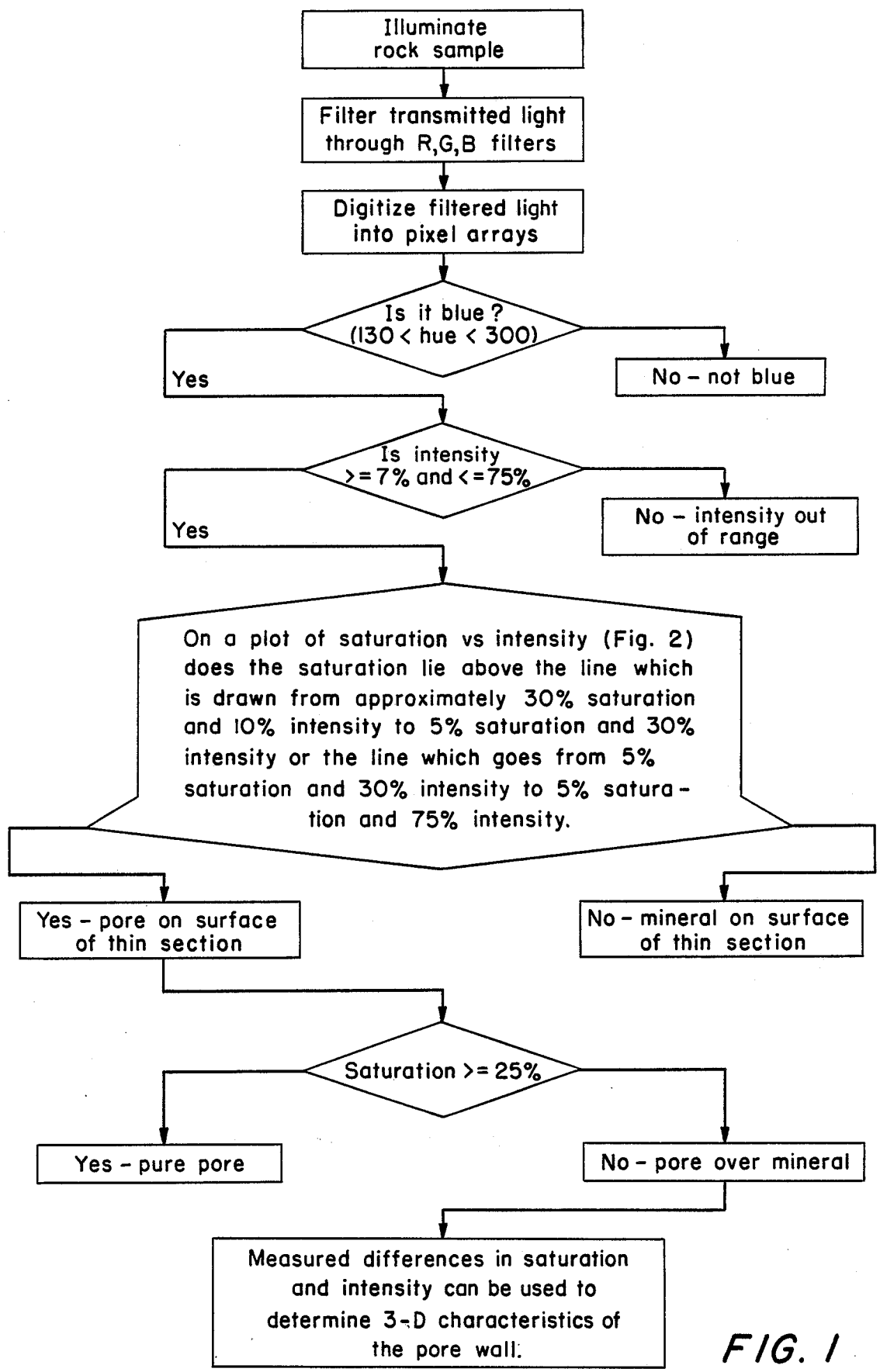
FIG. 1 is a flow chart of the preferred segmentation process carried out after the conversion of the transmitted light into pixels representative of the red, blue and green color components in the transmitted light.
Figure 2:
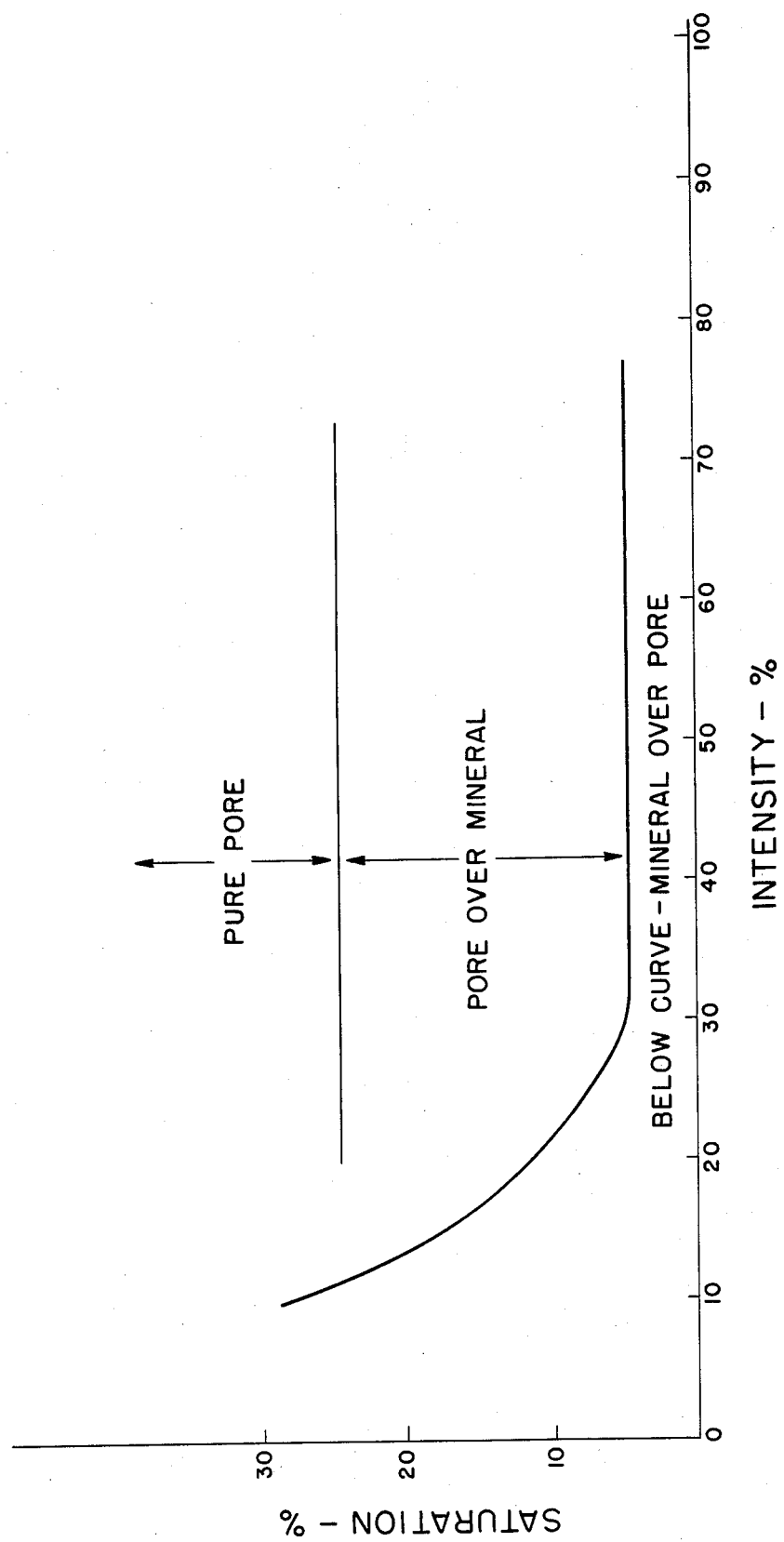
FIG. 2 is a plot of color intensity against color saturation used as a basis for one of the steps in the segmentation process of the present invention.

In a system such as that disclosed in our co-pending patent application Ser. No. 524,022 entitled "Analysis of Reservoir Pore Complexes," the initial image is a 30 micron thick section of a reservoir rock previously impregnated with a blue-dyed epoxy. The thin section is illuminated and the transmitted light is passed sequentially through red, blue and green filter gels which provide maximum enhancement to the blue-dyed epoxy-filled pores while leaving the background minerals relatively unchanged.

The light transmitted through each of the filters is digitized into an array of grid points or pixels. Each pixel is defined by its spatial coordinates and an intensity value which is a measure of the brightness of the transmitted red, blue or green light, as the case may be, at a given point in the image. As is well known, the number of pixels required to faithfully represent the image depends on both the overall size of the image and the size of the fine detail in it. Typical arrays for the purpose of the applicant's invention include 256,000 pixels for each image in each of the primary colors.

In order to classify the color components in a scene, it is necessary to have some system against which an unknown color can be compared. The first standardized color system was developed by Munsell in the 1920's. This color specification system includes a set of samples to serve as the standard. The Munsell color system can be thought of as a color solid in which all possible colors can be reproduced.

One way to describe this color system is to begin with a color wheel representative of a horizontal slice through the color solid. On the outer edge of the color wheel are the three primary colors which are pure colors at three points on the outer rim separated by 120°. Any point on the edge therefore is either a pure primary color or at most a combination of two of the three primary colors, i.e., red and blue, red and green, or blue and green.

Away from the edge, all points, as one approaches the center of the color wheel, become combinations of the three primary colors. At the center of the color wheel, there are equal amounts of red, green and blue. This combination yields achromatic color whose only attribute is its intensity. Depending upon the light intensity, it ranges from black (0% intensity) to white (100% intensity) with various levels of gray in between.

The Munsell color solid is created by combining hue, brightness and saturation. The color solid can be throught of as a stack of color wheels in which the wheel of maximum radius is found at approximately 50% brightness and the wheels of minimum radius are found at both 0% brightness and 100% brightness. The location of a wheel is determined by its brightness attribute.

The Munsell color solid was designed in a slightly pear-shaped form. Hue is an approximation to the wavelength of light and is used to distinguish between different colors, like red and green. Saturation is a measure of the lack of whiteness in a color and is used as a measure of how strong a color appears. Brightness is defined as the physical intensity.

Looking at the color wheel, which is a slice at some given brightness on the Munsell color solid, the saturation ranges from fully unsaturated at the center of the wheel to fully saturated at the edge. Therefore, a fully saturated color is one in which the relative amount of one or two of the primary colors are very near or at zero. The hue is expressed as an angle around the wheel from 0°–360°. Blue, for example, is defined from 181°–299° with pure blue being located at 240°. Brightness ranges from black to white.

There are two ways of producing color: additive color and subtractive color. The additive color reproduction system makes use of transmitted light in which the three primary colors are projected onto a common region on the screen to reproduce a colored light. Subtractive color systems are primarily used in photography, painting, etc., where colored dyes are mixed. With the subtractive color system, the dyes themselves absorb some of the light and the amount of absorpotion is dependent upon the dye concentration. Since this invention involves transmitted light, the system for comparison should be an additive color reproduction system.

The Munsell color system is difficult to reproduce on a computer. As a result, several other systems have evolved which can be recreated on color monitors. One of these is the HLS (hue, brightness and saturation) model used by Tektronix and based on the Ostwald color system. As described in *Fundamentals of Interactive Computer Graphics*, published by Addison-Wesley Publishing Company, at p. 617, the Ostwald color system makes use of a double hexcone. As in the HLS model, the double hexcone can be deformed into two cones to provide more even flow to the hue as one goes around the color wheel. Also, since it is difficult to define brightness in mathematical terms, intensity is used as the level of brightness. Hue, saturation and intensity are a convenient method for representing human color perception.

According to his invention, the following three formulas for calculating hue, intensity and satration are used. The first formula, which is used for calculating hue is set forth in a report by John R. Kender of the Department of Computer Science, Carnegie-Mellon University, Pittsburgh, Pa., entitled *Saturation, Hue and Normalized Color: Calculation, Digitization Effects, and Use* (November 1976). The formula is as follows:

$$\text{hue: } = \text{if } R > B \text{ and } G > B \text{ then} \quad (1)$$

$$pi/3 + \arctan(sqrt(3)\ (G - R)/(G - B + R - B))$$

else if $G > R$ then $$pi + \arctan(sqrt(3)\ (B - G)/(B - R + G - R))$$

else if $B > G$ then $$5pi/3 + \arctan(sqrt(3)\ (R - B)/(R - G + B - G))$$

else if $R > B$ then

0 else achromatic:

Intensity is claculated by use of the following formula:

$$\text{Intensity} = R + G + B \quad (2)$$

Saturation is calculated using the following formula:

$$\text{Saturation} = (1 - (3 * \text{Minimum }(R,G,B)) / \text{Intensity} \quad (3)$$

The pore to be separated from the scene is a rather medium blue except along the edge of the pore and through the pore throats where the blue-dyed epoxy may be impregnated into clay. The color of the blue also changes along the edge of the pore when shelving effects take place. Depending upon the mineral(s) in the shelf, the epoxy may show a significant difference from the pure epoxy in the center of a pore. In many cases, this change of color of the epoxy is only a change in the saturation.

From the foregoing equations, segmentation of the pores from the non-pores in each thin section of reservoir rock is achieved in the manner shown in the flow chart of FIG. 1. First, the pixels that are defined by the hue algorithm as located between 180° and 300° on the color wheel and therefore contain in them the color blue are isolated. Next, the blue pixels that are below 7% intensity and above 75% intensity are eliminated as representative of the colors black and white, respectively.

Saturation and intensity are then related through the following relationship. As intensity varies between 10 and 30%, the minimum saturation varies linearly from 30 to 5%. In the intensity range from 30 to 75%, the minimum saturation is 5%. Any pixels that fall outside these ranges are then removed as they are representative of pores overlain with minerals.

For pure pore, the saturation will generally exceed 25%. The saturation for the epoxy which overlaps transparent or translucent minerals will show a small drop while that for mineral overlying the epoxy will show the lowest saturation level. The difference in saturation and intensity can be used to determine the three-dimensional characteristics of the pore wall.

This procedure can, by using saturation, determine pore beneath mineral with saturation decreasing as the thickness of overlying mineral increases. Thus a three-dimensional characterization of the pore network can be determined. This is true for all three-dimensional complexes composed of differently colored transparent to translucent components. It thus should also be effective in biological imaging and other fields.

The described digital filtering process has been used to segment the pores from the non-pores in a thin section of reservoir rock. Following such segmentation, the geometry of the pores is evaluated by the process described in our co-pending application Ser. No. 524,022.

It will be appreciated that the application of the segmentation process described in this application is not limited to the pores and minerals in a solid matrix of rock. Two disparate phases in a solid may be segmented in accordance with the disclosure of this application. For instance, a limestone may contain the minerals gypsum and calcite in the form of granular carbonate mud, fragments of fossil shells, and pieces of coral. Each of these phases, whether defined by mineralogy or by mode of formation can be segmented by the use of the digital filter described in this application, just as pores are segmented from the rock matrix.

I claim:

1. A process for segmenting one state from one or more other states made up of pores and minerals in a reservoir rock sample comprising the steps of impregnating the sample with a pigmented plastic material to provide an observable color characteristic, illuminating the sample with light, passing the light transmitted by the sample through a plurality of color filters to provide filtered images of different color components, converting density levels in the filtered images into scene pixels, calculating hue from the different color components in each scene pixel, comparing the calculated hue against the hue of an observable color characteristic of the one state and separating the pixels based on the correspondence between the calculated hue and the hue of the observable color characteristic of the one state.

2. A process according to claim 1 wherein at least one of said filters corresponds to the color of characteristic, the one state.

3. A process according to claim 2 wherein the pores in the sample are impregnated with a blue-dyed epoxy.

4. A process according to claim 3 wherein the light transmitted by the reservoir rock sample is passed through red, green and blue filters to develop scenes of the reservoir rock sample in red, blue and green components, and wherein hue is calculated from the red, blue and green components in each scene pixel.

5. A process according to claim 4 wherein the scene pixels are separated based on a calculated angularity for hue which falls inside the range of 180° to 300°.

6. A process according to claim 5 comprising the further steps of summing the red, blue and green components in each of the separated pixels and further separating those pixels having intensities which range between approximately 7% and 75%.

7. A process according to claim 6 comprising the further steps of measuring the saturation of the further separated pixels and still further separating the pixels having at least 5% saturation through a range of intensities from 30% to 75% and in excess of 30% to 5% saturation as intensities vary from 7% to 30%, respectively.

* * * * *

UNITED STATES PATENT AND TRADEMARK OFFICE
CERTIFICATE OF CORRECTION

PATENT NO. : 4,727,498
DATED : February 23, 1988
INVENTOR(S) : Ehrlich et al

It is certified that error appears in the above-identified patent and that said Letters Patent is hereby corrected as shown below:

On the title page

The A. Ruter et al reference should be included in the references cited portion of the patent.

Col. 4, line, "satration" should read -- saturation --.

Signed and Sealed this

Thirtieth Day of August, 1988

Attest:

DONALD J. QUIGG

*Attesting Officer*   *Commissioner of Patents and Trademarks*